United States Patent
Naundorf et al.

(10) Patent No.: US 6,177,255 B1
(45) Date of Patent: Jan. 23, 2001

(54) METHOD FOR DETECTING A HORMONE OR ANTIHORMONE RESISTANCE IN CANCERS

(75) Inventors: Helga Naundorf; Claudia Neumann, both of Bernau; Iduna Fichtner; Michael Becker, both of Berlin, all of (DE)

(73) Assignee: Max-Delbrück-Centrum für Molekulare Medizin (DE)

( * ) Notice: Under 35 U.S.C. 154(b), the term of this patent shall be extended for 0 days.

(21) Appl. No.: 09/214,805
(22) PCT Filed: Jul. 5, 1997
(86) PCT No.: PCT/DE97/01423
  § 371 Date: Feb. 22, 1999
  § 102(e) Date: Feb. 22, 1999
(87) PCT Pub. No.: WO98/02747
  PCT Pub. Date: Jan. 22, 1998

(30) Foreign Application Priority Data

Jul. 12, 1996 (DE) .............................................. 196 28 298

(51) Int. Cl.[7] ..................... G01N 33/53; G01N 33/567; G01N 33/576; C12Q 3/00; C12Q 1/00
(52) U.S. Cl. ..................................... 435/7.1; 435/4; 435/3; 435/7.2; 435/7.21; 435/7.23; 435/7.7; 435/7.72; 435/7.8; 435/7.9; 435/7.92; 435/7.93; 435/7.94; 435/28
(58) Field of Search ............................ 435/7.1, 4, 3, 7.2, 435/7.21, 7.23, 7.7, 7.72, 7.8, 7.9, 7.92, 7.93, 7.94, 28; 424/138.1, 141.1, 163.1

(56) References Cited

U.S. PATENT DOCUMENTS 5,292,638 * 3/1994 Benz et al. ................................ 435/6

FOREIGN PATENT DOCUMENTS 0 129 669 * 2/1985 (EP) .............................. G01N/33/74

OTHER PUBLICATIONS

Y. Berthois, et al.; Agonist–antagonist activity of anti–estrogens in the human breast cancer cell line MCF-7: an hypothesis for the interaction with a site distinct from the estrogen binding site; Molecular and Cellular Endocrinology, 99(1994) pp. 259–268.

A. Wakeling; Are breast tumours resistant to tamoxifen also resistant to pure antioestrogens?; J. Steriod Biochem. Molec. Biol. vol. 47, No. 1 6, pp. 107–114 1993.

(List continued on next page.)

Primary Examiner—Jeffrey Stucker
Assistant Examiner—Brett Nelson
(74) Attorney, Agent, or Firm—Norris, McLaughlin & Marcus P.A.

(57) ABSTRACT

The invention concerns a method for detecting a hormone or antihormone resistance in cancers. The invention is intended for use in medicine, biology and the pharmaceutical industry. The aim of the invention is to consistently improve the use of antihormones in the treatment of cancer so that unnecessary treatment can be avoided as much as possible. The aim is to develop a method which can be used to identify the type of cancer before corresponding antihormone treatment is given. This aim is achieved by measuring the immune reactivity of the hormone receptors of cancers. The method as per the invention is characterized in that an antihormone receptor antibody, which is attached to a solid, is incubated with a prepared cytosol from the cancer tissue being investigated and, following removal of the liquid, is once again incubated with the addition of the respective hormone or antihormone, then a second enzyme-labelled antibody is added, the color reaction measured and the determined value for the immune reaction is compared with the control value which is obtained in the same way but without the respective hormone or antihormone being incubated.

5 Claims, 1 Drawing Sheet

OTHER PUBLICATIONS

G. Williams et al.; Long–term prophylactic use of tamoxifen: is it safe?; European Journal of Cancer Prevention, vol. 1 1992 pp. 386–387.

J. Harris et al.; Breast Cancer (Third of Three Parts); New England Journal of Medicine, vol. 327, No. 7 Aug. 13, 1992 pp. 473–480.

J. Harris et al.; Breast Cancer (First of Three Parts); New England Journal of Medicine, vol. 327, No. 5 Jul. 30, 1992 pp. 319–328.

H. Naundorf et al.; Establishment and characterization of a new human oestradiol–and progesterone–receptor–positive mammary carcinoma serially transplantable in nude mice; J. Cancer Res.Clin.Oncol. 1992 119: pp. 35–40.

Berthois et al.; Agonist–antagonist activity of ani–estrogens in the human breast cancer .... ; Molecular and Cellular Endocrinology; vol. 99; pp. 259–268, 1994.*

Harlow et al.; Antibodies a laboratory manual; pp. 578–581, 1988.*

Lippman et al.; Current concepts in cancer– receptors in breast cancer; The New England journal of Medicine; vol. 299, No. 17; pp. 930–933, Oct. 1978.*

* cited by examiner

METHOD FOR DETECTING A HORMONE OR ANTIHORMONE RESISTANCE IN CANCERS

This application is a national stage entry of PCT/DE97/01423, filed Jul. 5, 1997.

BACKGROUND OF THE INVENTION

The invention concerns a method for detecting a hormone or antihormone resistance in tumours. The invention is intended for use in medicine, biology and pharmaceutical industry.

Tumours in organs depending on hormones such as in the breast and ovaries are tumour diseases met most frequently in women in industrialized countries. Thus, in about 12% of the female population breast cancer is diagnosed, with the peak of sickening being between the $4^{th}$ and $6^{th}$ decade of life. 3.5% of women die of it (Harris et al., New England J Med 327: 319–328, 1992).

Depending on the stage at which breast cancer is diagnosed the chances of recovery are between 30 and 70%. As about ⅔ of the tumours detected have hormone receptors these patients are given hormone preparations as primary medication. They are to competitively displace the natural ligand (oestrogen) from the receptor, thus affecting the growth of the tumours caused by hormones. Tamoxifen, a non-steroidal antioestrogen, is most frequently used for treating mammary carcinomas with the adjuvant use to prevent the development of metastases, yet also the prophylactic use for patients with a family-connected risk (Harris et al., New England J Med 327: 473–480, 1992).

It is known that about only half of the hormone receptor-positive patients respond to a tamoxifen therapy. This raises questions relating to the principle action of antioestrogens which, for the time being, are still largely unclarified. Thus, Berthois et al. (Molecular and cellular Endocrinology 99: 259–268, 1994) described that the immune reactivity of oestroqen receptors to an antibody will increase if oestradiol or tamoxifen are added in a cytosole test. The authors discuss a change of conformation of the oestrogen receptor by an in vitro interaction with hormones and anti-hormones as a potential mechanism for an apparent increase of the positions for the epitope binding.

Though tamoxifen is comparatively well-tolerated also in long-term use its possible cancerogenic potential has been discussed recently (Williams et al., Eur J Cancer Prev 1: 386–387, 1992).

SUMMARY OF THE INVENTION

The invention is aimed at improving the use of antihormones for the therapy of tumours in order to avoid unnecessary therapies as far as possible. Its aim is to develop a method which allows to predict the response of a tumour before applying a respective antihormone therapy.

Starting point of the invention is the surprising finding that the immune reactivity of sensitive and at resistant tumours differs given specific conditions of reaction. If hormone receptors contained in the tumour are bound to an antibody, in the case of sensitive tumours, their inmmune reactivity is increased by adding respective hormones or antihormones, however not in the case of resistant tumours. That means, the positions of epitope binding are apparently increased only in the case of sensitive tumours.

This effect has been used for designing the method according to the invention wherein an antihormone receptor antibody bound to a solid phase is incubated with cytosole prepared of the tumour tissue under investigation, the liquid is subsequently removed and adding the appropriate hormones or antihormones a repeated incubation i s performed and subsequently a second enzyme-labelled antibody is added, the colour reaction is measured and the value determined for the immune reaction is compared with the control value determined in the same way, but without incubation with the appropriate hormones or antihormones.

In this description n we understand by hormones oestrogens (such as 17β-oestradiol), progesterone or androgen, by antihormones antioestroqens (such as tanoxifen or 4-hydroxy-tamoxifen), antiprogestins or antiandrogens (such as cyproteronacetate).

PREFERRED EMBODIMENTS OF THE INVENTION

Figure 1:
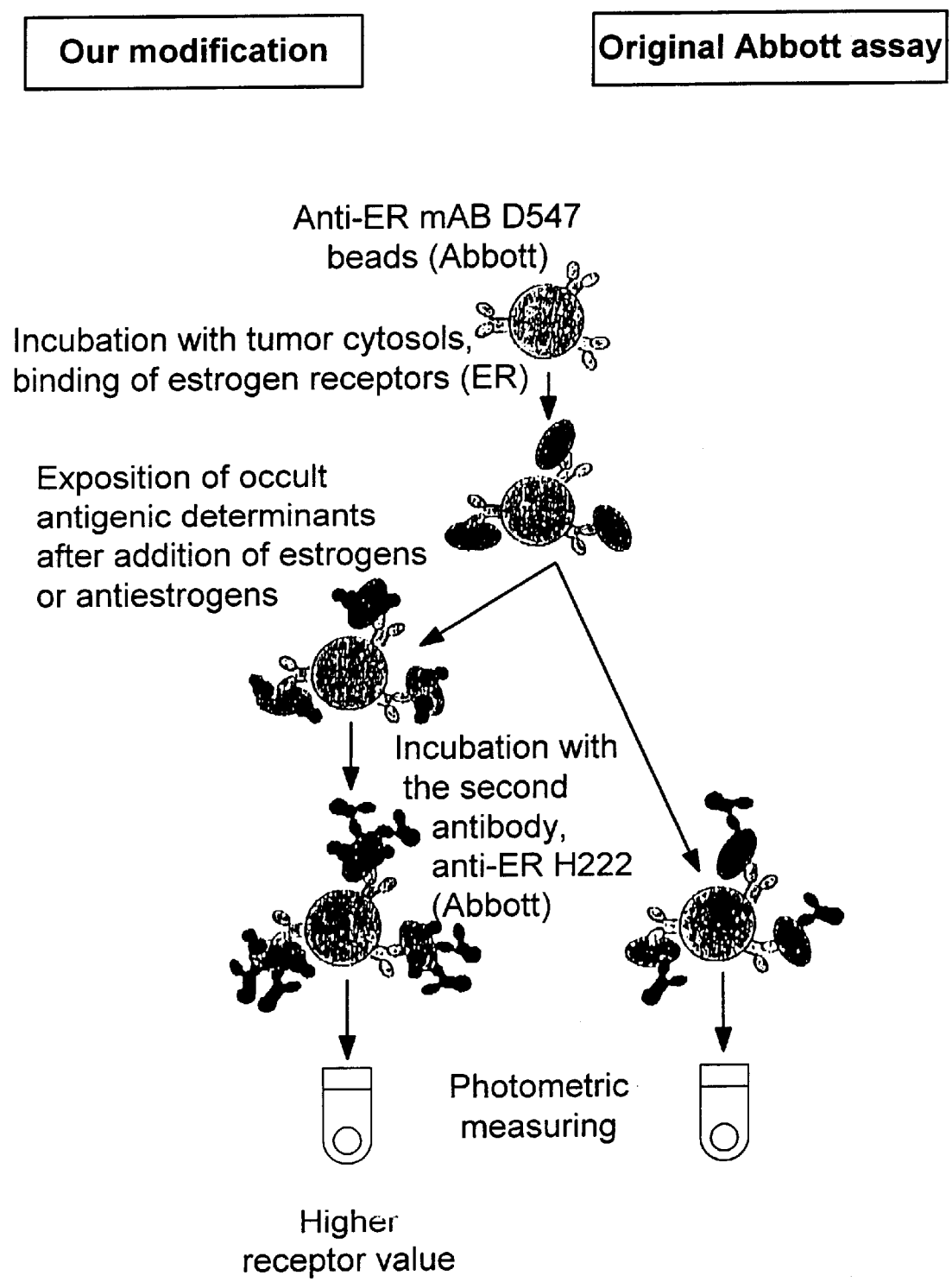
FIG. 1—diagram of the method of the present invention for detecting a hormone or antihormone resistance in cancers.

The method is, in particular, described by means of the oestrogen example. We use a commercial enzyme immunoassay which in clinical routine is used for determining hormone receptors. Polystyrene beads covered by an anti-oestrogen receptor antibody will be incubated with cytosole prepared of the respective tumour tissues. After binding of the available oestrogen receptors to the primary antibody the liquid is removed. After adding oestrogens or antioestrogens such as tamoxifen the mixture is incubated repeatedly. Then, a second peroxydase-coupled antibody is added and its colour reaction is measured which allows a direct calculation of the available oestrogen receptor (FIG. 1).

The invention allows a reliable differentiation between sensitive and resistant tumours and thus an assessment of the chances of success of an antitumoural hormone therapy.

The invention is explained in greater detail hereinafter by an example of execution:

EXAMPLE

The results are based on experiments carried out with a hormone receptor-positive mammary carcinoma (3366) established from patients' material as a xenotransplantation model on nude mice (H. Naundorf et al., J. cancer Res Clin Oncol 119: 35–40,1992). By treating this tumour which was originally extremely sensitive to tamoxifen in vivo with suboptimal doses for a few years a resistant subline was produced.

The tumours of the mammary carcinoma 3366 are shock-frozen and preserved in liquid nitrogen until the test will be carried out. By means of ultra-sound the samples are homogenized at 2–8° C. 5 times in an ice bath (10 sec.).

Cytosoles of the tamoxifen-sensitive and the tamoxifen-resistant lines are used in the enzyme immunoassay developed by the Abbott company. This enzyme immunoassay contains the antioestrogen receptor antibody D547 and the peroxidase-coupled antibody H222 as second antibody the colour reaction of which is measured after adding o-phenyldiamine at 492 nm. The cytosole is prepared according to the instruction enclosed in the Abbott ER-EIA monoclonal kit and the protein content is set to 1–2 mg/ml.

After incubation with antibody beads (D 547) the liquid is sucked off by means of a quick-wash facility (Abbott) in 8–12 ml of distilled water. Always 200 ml of the receptor hormone or antihornone are pipetted to the beads as a double determination. 4-hydiroxytamoxifen, 17 β-estradiol, ICI 182,780 (Wakeling, J. Steroid Biochem Molec Biol 47: 107–114, 1991) and progesteron in concentrations between $10^{-4}$ and $10^{-10}$ molar are used. The most optimum results are obtained with $10^{-6}$ molar, aqueous solutions prepared of a $10^{-4}$ molar ethanolic solution. In the control sample only solvent is used without adding hormones.

The residence time of the hormones or antihormones at the beads is 2 hours, the temperature 37° C. (incubator).

Thereupon, the liquids are again sucked off by means of the quick-wash and with the second antibody H222 being added. After reaction with the o-phenyldiamine hydrochloric acid solution the ER receptors are measured according to the Abbott instruction in fmol/ml or extinction at 492 nm.

The results are summarised in the following table:

Immune reactivity (in percent) to antibody H222:

|  | mammary carzinoma 3366 | |
| --- | --- | --- |
| Treatment | tamoxifen-sensitive | tamoxifen-resistant |
| without | 100 | 100 |
| 4-hydroxytamoxifen | 262 ± 53' | 140 ± 13 |
| 17b-oestradiol | 243 ± 45' | 116 ± 17 |
| ICI 182, 780 | 291 ± 100+ | 123 ± 5 |
| progesteron | 91 ± 8 | 93 ± 10 |

(*significant as compared with the resistant line)

The results show that the immune reactivity increases significantly only in (anti)hormone-sensitive tumours whereas in resistant tumours additional antibody binding positions are not presented. Thus, this test method may be applied to distinguish between hormone and antihormone sensitive and resistant tumours.

Legend of FIG. 1

1—Incubation with tissue cytosoles, binding of the oestrogen receptor

2—Adding of oestrogens or antioestrogens

3—Incubation with a second antibody

4—Photometric measurement

5—Increased receptor value=sensitive tumour

6—Normal receptor value=resistant tumour

What is claimed is:

1. A method for detecting hormone resistance or antihormone resistance in tumors, comprising the following steps, in sequence:

(a) obtaining cytosol from tumor tissue thereby producing a liquid sample, (b) contacting the cytosol with an antihormone receptor antibody to form a complex, (c) removing the liquid, (d) incubating the complex with a hormone or antihormone, (e) contacting the complex with an enzyme labeled antibody, and (f) measuring the degree of immune reaction as indicated by a resulting color change, and comparing it to a control, thereby determining whether the tumor tissue is either sensitive or resistant to hormones or antihormones.

2. The method of claim 1, wherein the antihormone receptor antibody is antioestrogen receptor antibody.

3. The method of claim 2, wherein hormone or antihormone is chosen from the group consisting of oestrogen, tamoxifen and antioestrogen.

4. The method of claim 1, wherein the enzyme labeled antibody is peroxidase-coupled antibody.

5. The method of claim 1, wherein step (d) is carried out with a $10^{-6}$ to $10^{-7}$ molar solution of the hormone or antihormone.

* * * * *